United States Patent [19]

Christensen

[11] Patent Number: Plant 5,998

[45] Date of Patent: Sep. 1, 1987

[54] HYBRID SHRUB ROSE PLANT CV. AROPICLU

[75] Inventor: Jack E. Christensen, Ontario, Calif.

[73] Assignee: Armstrong Nurseries, Inc., Somis, Calif.

[21] Appl. No.: 773,660

[22] Filed: Sep. 9, 1985

[51] Int. Cl.[4] ..... A01H 5/00

[52] U.S. Cl. ..... Plt./1

[58] Field of Search ..... Plt./1

*Primary Examiner*—Robert E. Bagwill

*Attorney, Agent, or Firm*—Synnestvedt & Lechner

[57] ABSTRACT

A new hybrid shrub rose for garden decoration, having as its seed parent the hybrid floribunda rose Zorina (U.S. Plant Pat. No. 2,321) and as its pollen parent an undisseminated, open-pollinated seedling of Gartendirektor Otto Linne. The new cultivar produces extremely abundant quantities of unusually shaped, small, coral pink flowers that are borne in very large pyramidal clusters and are produced almost continuously throughout the growing season. Foliage is narrow and elongated, with highly serrated edges. The plant's growth habit is semi-pendulous, yielding a large, well-filled and rounded bush with flowers and foliage extending to the ground. It is a low-maintenance plant, displaying female sterility and well-above-average disease resistance.

1 Drawing Figure

This invention relates to a new and distinct variety of hybrid shrub rose cv. Aropiclu. The plant is a hardy outdoor seedling, cultivated for garden decoration, which produces a bush of medium height for the class. It was bred by Jack E. Christensen in Ontario, Calif., and has as its seed parent Zorina (U.S. Plant Pat. No. 2,321) and as its pollen parent an undisseminated, open-pollinated seedling of Gartendirektor Otto Linne.

The new variety cv. Aropiclu may be distinguished from other presently available commercial rose cultivars by the following combination of characteristics: its unusual open flower form, which is not often associated with roses of this class, essentially as described and illustrated herein; its extremely abundant production of flowers in very large pyramidal clusters; its female sterility and well-above-average disease resistance, which make the plant a low-care rose, requiring little maintenance to produce an attractive bush; its semi-pendulous branching habit, yielding a large, well-filled and rounded bush with flowers and foliage extending to the ground; its very narrow, elongated foliage with highly serratd edges; and its nearly continuous production of flowers throughout the growing season.

The new rose may be distinguished from its seed parent, Zorina, by the following combination of characteristics: Whereas the seed parent bears flowers of a distinctly orange coloration, Aropiclu bears flowers of a coral pink coloration, essentially as described and illustrated herein. Zorina is a hybrid floribunda rose, bred and used predominantly for greenhouse cut flower production, whereas the new seedling is a hybrid shrub, useful only for garden decoration. The new cultivar bears flowers in large pyramidal clusters, whereas the seed parent produces significantly smaller flower clusters. The branching habit of Aropiclu is semi-pendulous, whereas the branches of Zorina are significantly stronger and erect.

Aropiclu may be distinguished from Gartendirektor Otto Linne (the cultivar from which its pollen parent was obtained as an undisseminated open-pollinated seedling), by the following combination of characteristics: Gartendirektor Otto Linne produces flowers of a pink coloration with darker edges, whereas the new cultivar produces flowers of a relatively uniform pink coloration with coral overtones, essentially as described and illustrated herein. Aropiclu produces a large, rounded and well-branched bush, whereas Gartendirektor Otto Linne produces a significantly larger, more rambling mature bush.

The accompanying drawing illustrates the plant in color and shows the flowering thereof from bud to full bloom. Throughout this specification, color names beginning with a small letter signify that the name of that color as used in common speech is aptly descriptive. Color names beginning with a capital letter designate values based upon The R.H.S. Colour Chart of The Royal Horicultural Society of London, England.

The descriptive matter which follows pertains to roses of the new variety grown in southern California and is believed to apply to plants of the variety grown in similar conditions of soil and climate elsewhere.

FLOWER

The new variety usually bears its flowers several to a stem, in regular, pyramidal clusters. Flowers are borne on weak to normal stems that are of medium length for the class. Outdoors, the plant blooms very abundantly and continuously during the growing season. The flowers have a slight apple fragrance.

BUD

The peduncle is erect, of short to average length for the class, and of average caliper. It is usually rough and covered with numerous stipitate glands and small hairs. The color of the peduncle is between Yellow-Green 144A and Green 139A, washed heavily with near Greyed-Purple 183C.

Before the calyx breaks, the bud is small for the class, long and pointed, with a conspicuous neck. There are a few foliaceous appendages and many stipitate glands on the surface of the bud. Slender, entire foliaceous parts are usually present, extending beyond the tip of the bud and equalling one half or more of its length.

As the calyx breaks, bud color is between Red 47A and Red 43A.

The inner surface of the sepals has a fine, woolly tomentum; margins are lined with hairs.

As the first petal opens, the bud is small for the class, long and pointed to urn-shaped in form. Both the inside and outside surfaces of the opening petals are between Red 47B and Red 43B in color. The bud opens up well and is not prevented from opening by cold, hot, wet, or dry weather.

BLOOM

When fully open, the bloom is small to average in size for the class, ranging from 1½ to 2 inches in diameter. Petalage is semi-double, with petals arranged irregularly; there are from 16 to 20 petals present and from 2 to 10 petaloids. When half open, the bloom is somewhat high-centered to cupped in form, and the petals are moderately cupped with flat edges. When fully open, the bloom is somewhat semi-flat to cupped, with petals more cupped and petal edges moderately reflexed outward to flat.

The petals are moderately heavy and crisp, of medium thickness, with insides and outsides slightly satiny. The outside petals are nearly obovate in shape, with mucronate apices. The intermediate petals are narrowly obovate with mucronate apices. The inner petals are narrowly obovate with mucronate apices. Petal colors may be modified by being shaded or washed or tinted with other colors.

The paragraph immediately following describes the color values observed in a newly opened flower on a plant grown outdoors in Ontario, Calif., in the month of October.

The outside surface of the outside, intermediate and inner petals displays a small basal attachment zone near Yellow 2D which quickly suffusses to between Red 51B and Red 50B. The inside surface of the outside, intermediate and inner petals displays a larger basal attachment zone near Yellow 2D which slowly suffuses to between Red 52B and Red 50B.

The paragraph immediately following describes the color values observed in a bloom which had been open for three days in the month of October. The plant described had been grown outdoors in Ontario, Calif.

The outside surface of the outside and inside petals displays a small basal attachment zone near White 155D in color, which quickly suffuses to between Red 51A and Red 47D. The inside surface of the outside and inside petals displays a larger basal attachment zone near White 155D which slowly suffuses to between Red 52B and Red 47B.

The general color effect of the newly opened flower is between Red 50B and Red 52B. After being open three days, the bloom gives a general color effect that is between Red 52B and Red 47B. The petals persist and are not particularly affected by cold, hot, wet, or dry weather.

In October, flowers on plants of the new variety grown in the garden last on the bush from 4 to 5 days; flowers cut from plants grown outdoors last from 6 to 7 days at living-room temperatures.

REPRODUCTIVE ORGANS

Stamens are few to average in number and are arranged regularly about the pistils; a few are mixed with petaloids. The filaments are short to medium in length, and most have anthers. The anthers are of medium size, and all open at approximately the same time. Anther color is near Yellow-Orange 23B when immature and near Greyed-Orange 166A at maturity. Pollen is very sparse and near Yellow 2D in color.

Pistils are few, numbering approximately 12. The styles are uneven, short to average in length, of average caliper, and somewhat loosely bunched. The stigma is near Yellow 2C in color.

The new variety Aropiclu does not normally set hips under Ontario, Calif. growing conditions.

FOLIAGE

The compound leaves are borne in very abundant quantities and usually comprise from five to seven leaflets. The leaves are of medium size for the class, heavy to somewhat leathery, and semi-glossy. The leaflets are oblong to nearly lanceolate in shape, with acute apices and acute bases; their margins are irregularly serrate.

The upper surface of the mature foliage is between Yellow-Green 146A and Green 136A in color; its under surface is near Green 138C. The upper surface of the young foliage is between Yellow-Green 144A and Green 136A, washed heavily with near Greyed-Purple 183C. The under surface of the young foliage is near Greyed-Purple 183D.

The rachis is average in size, grooved on its upper side, and has some stipitate glands on its edges. The under side of the rachis is sparsely prickly.

Stipules are long, moderately narrow, and have medium-length to long points turning out at an angle of less than 45°.

The plant displays a more-than-average resistance to mildew, rust and blackspot as compared to other commercial varieties grown under comparable conditions in Ontario, Calif.

GROWTH

The plant is of medium height for the class, much branched, bushy and compact, and of upright to pendulous habit. Its growth is very vigorous. The canes are of medium caliper for the class.

The main stems are between Green 137A and Yellow-Green 146A in color. They bear several large prickles which are of medium length for the class. The large prickles are almost straight, with medium-length, moderately broad bases; prickle color is near Greyed-Orange 165B. The main stems bear a few small prickles, also near Greyed-Orange 165B in color, and have no hairs.

The branches are of a color between Green 138B and Green 133A. They bear several large prickles of medium length for the class, which are almost straight and have medium-length, moderately broad bases. Their color is near Greyed-Orange 163C. The branches have several small prickles near Greyed-Orange 163C in color and no hairs.

New shoots are near Greyed-Purple 183D in color. They bear several large prickles of medium length for the class, which are almost straight with medium-length, moderately broad bases. Prickle color is near Greyed-Purple 185A. There are several small prickles near Greyed-Purple 185A in color and no hairs.

I claim:

1. The new and distinct variety of hybrid shrub rose plant cv. Aropiclu and the parts thereof, substantially as shown and described herein, the plant being particularly characterized by its unusual open flower form, essentially as described and illustrated herein; its extremely abundant production of flowers in very large pyramidal clusters; its female sterility and well-above-average disease resistance; its semi-pendulous branching habit, yielding a large, well-filled and rounded bush with flowers and foliage extending to the ground; its very narrow, elongated foliage with highly serrated edges; and its nearly continuous production of flowers throughout the growing season.

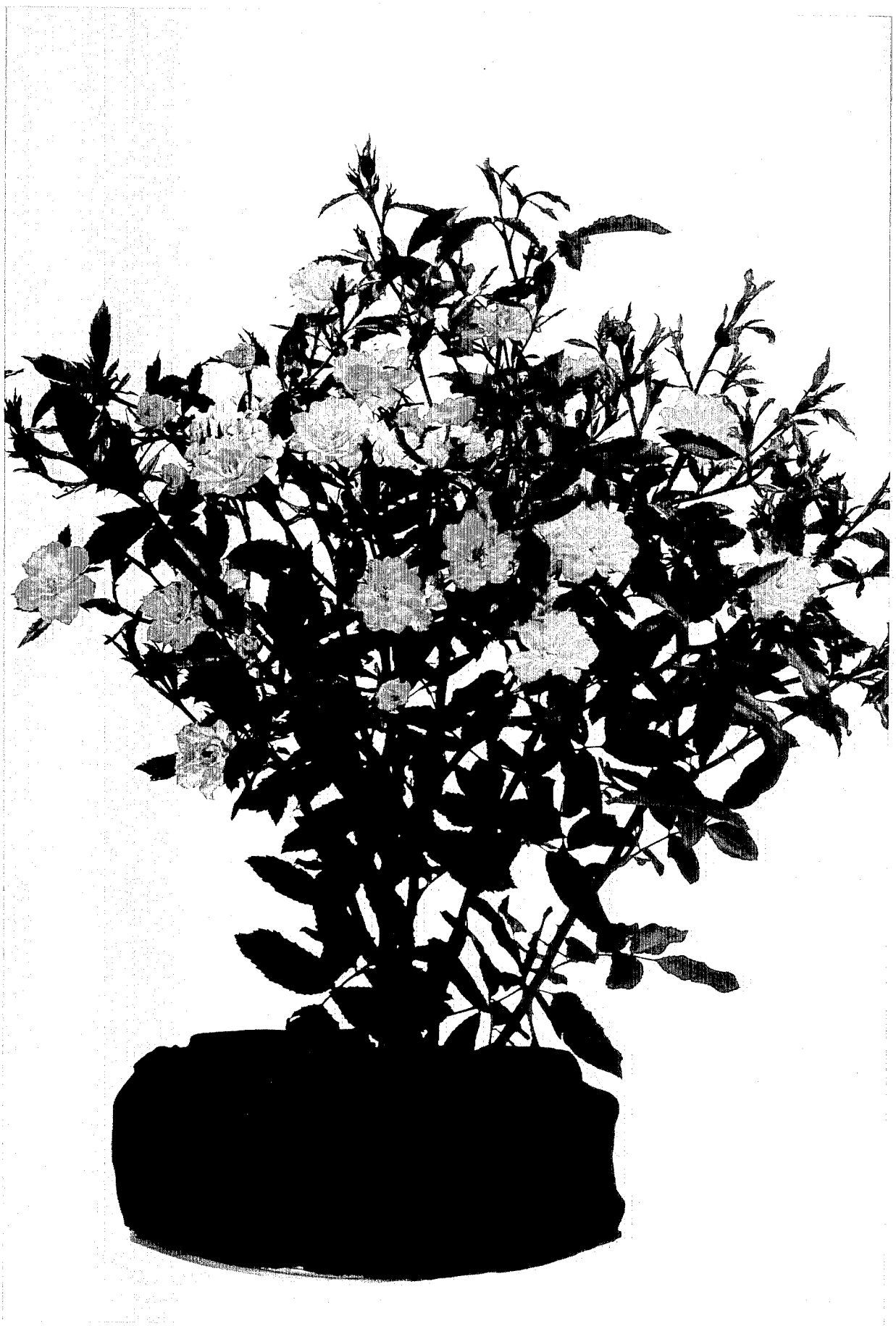

* * * * *